United States Patent
Mouazer et al.

(10) Patent No.: US 9,533,885 B2
(45) Date of Patent: Jan. 3, 2017

(54) PROCESS TO SEPARATE PHOSGENE AND HYDROGEN CHLORIDE FROM A FLUID STREAM COMPRISING PHOSGENE AND HYDROGEN CHLORIDE

(75) Inventors: Rabah Mouazer, Wavre (BE); Ramon Scheffer, Baton Rouge, LA (US)

(73) Assignee: Huntsman International LLC, The Woodlands, TX (US)

( * ) Notice: Subject to any disclaimer, the term of this patent is extended or adjusted under 35 U.S.C. 154(b) by 118 days.

(21) Appl. No.: 14/117,892

(22) PCT Filed: Jun. 15, 2012

(86) PCT No.: PCT/EP2012/061395
§ 371 (c)(1),
(2), (4) Date: Nov. 15, 2013

(87) PCT Pub. No.: WO2013/026591
PCT Pub. Date: Feb. 28, 2013

(65) Prior Publication Data
US 2014/0147373 A1     May 29, 2014

(30) Foreign Application Priority Data
Aug. 19, 2011    (EP) .................................... 11178124

(51) Int. Cl.
*C07C 263/10*     (2006.01)
*C07C 263/20*     (2006.01)
(Continued)

(52) U.S. Cl.
CPC ............. *C01B 7/0706* (2013.01); *B01D 53/22* (2013.01); *C01B 31/28* (2013.01); *C07C 263/10* (2013.01); *B01D 2257/2045* (2013.01); *B01D 2257/2064* (2013.01); *C07C 263/20* (2013.01); *Y02P 20/154* (2015.11)

(58) Field of Classification Search
CPC ... C01B 7/0706; B01D 11/0415; B01D 53/22; B01D 53/228; B01D 2256/26; B01D 2257/2045; C07C 263/10; C07C 263/20
See application file for complete search history.

(56) References Cited

U.S. PATENT DOCUMENTS 5,891,319 A *   4/1999   Freire et al. .................. 205/499
7,584,629 B2     9/2009   Sohn et al.
(Continued)

FOREIGN PATENT DOCUMENTS

EP           1575906       9/2005
EP           1849767     10/2007
(Continued)

*Primary Examiner* — Wayne Langel
(74) *Attorney, Agent, or Firm* — Huntsman International LLC

(57) ABSTRACT

A process according to the invention is a process to separate an initial fluid stream comprising phosgene and hydrogen chloride in at least a first and a second fluid stream, said first fluid stream being a hydrogen chloride enriched and phosgene depleted gaseous stream, said second fluid stream being a hydrogen chloride depleted and phosgene enriched stream. The separation is performed by feeding said initial fluid stream to a membrane separation unit, said membrane separation unit separating said initial fluid stream in a first and a second fluid stream.

11 Claims, 7 Drawing Sheets

(51) Int. Cl.
*C01B 7/07* (2006.01)
*B01D 53/22* (2006.01)
*C01B 31/28* (2006.01)

(56) References Cited

U.S. PATENT DOCUMENTS

| | | | | |
|---|---|---|---|---|
| 8,114,192 | B2 * | 2/2012 | Baker | B01D 53/22 |
| | | | | 422/187 |
| 9,302,983 | B2 * | 4/2016 | Lehr | C01B 7/04 |
| 9,328,064 | B2 * | 5/2016 | Bruns | C07C 263/10 |
| 2007/0249859 | A1 | 10/2007 | Bohm et al. | |
| 2007/0261437 | A1 | 11/2007 | Boonstra et al. | |
| 2008/0168900 | A1 * | 7/2008 | Ho | C08G 61/06 |
| | | | | 95/48 |
| 2009/0209784 | A1 | 8/2009 | Lorenz et al. | |
| 2011/0166369 | A1 | 7/2011 | Krafft et al. | |
| 2013/0047844 | A1 * | 2/2013 | Zheng | B01D 67/003 |
| | | | | 95/45 |

FOREIGN PATENT DOCUMENTS

| | | |
|---|---|---|
| JP | 9131516 | 5/1997 |
| WO | 2010/029153 | 3/2010 |

* cited by examiner

PROCESS TO SEPARATE PHOSGENE AND HYDROGEN CHLORIDE FROM A FLUID STREAM COMPRISING PHOSGENE AND HYDROGEN CHLORIDE

CROSS-REFERENCE TO RELATED APPLICATIONS

This application is the National Phase of International Application PCT/EP2012/061395 filed Jun. 15, 2012 which designated the U.S. and which claims priority to European App. Serial No. 11178124.1 filed Aug. 19, 2011. The noted applications are incorporated herein by reference.

The present invention relates to processes for the conversion of an amine to the corresponding isocyanate component by phosgenation of the amine. In particular the invention relates to purification and/or separation of hydrogen chloride and phosgene in the effluent streams of such processes.

In processes where amines are converted to isocyanates using phosgene, as is well known in the art, a disadvantage is that in the phosgenation process, typically an excess of phosgene is used, or that the phosgenation typically does not consume all phosgene in the reaction mixture, while hydrogen chloride is obtained by the conversion of an amine group to an isocyanate group. Hence typically the reaction mixture, either gaseous or liquid, e.g. all components dissolved in a solvent, comprises phosgene and hydrogen chloride.

Often the hydrogen chloride is separated from the reaction, and can be used in other processes or as a recycle stream, provided the hydrogen chloride is purified to meet the needs of its further use.

Often there is a need to remove the phosgene from the hydrogen chloride, as is e.g. described in EP1575906A.

It is an object of the present invention to provide a process to separate phosgene and hydrogen chloride from a fluid stream comprising phosgene and hydrogen chloride, which process is less expensive in energy consumption. The process according to the invention may reduce the size or even avoid the need to use absorption towers, stripping columns, distillation towers and alike, to efficiently separate the phosgene from the hydrogen chloride. The process according to the invention may improve the yield and/or the efficiency of the separation of phosgene and hydrogen chloride in a continuous operation.

The process to separate hydrogen chloride from phosgene according to the invention may be less complex in design, may require less equipment and/or installation cost of equipment, and is less complex in use, as compared to conventional processes to remove hydrogen chloride from phosgene.

According to a first aspect of the present invention, a process to separate an initial fluid stream comprising phosgene and hydrogen chloride in at least a first and a second fluid stream, the first fluid stream being a hydrogen chloride enriched and phosgene depleted gaseous stream, the second fluid stream being a hydrogen chloride depleted and phosgene enriched stream, is provided. The separation is performed by feeding the initial fluid stream to a membrane separation unit, the membrane separation unit separating the initial fluid stream in the first and the second fluid stream. The membrane separation unit is provided with at least one inflow means and at least two effluent outflow means and comprises at least one separation cell, each cell having a feed and two output streams, being the retentate and the permeate of the cell.

In each cell, a fluid comprising phosgene and hydrogen chloride, is brought into contact with one side (the retentate side) of the membrane present in the cell, which membrane is permeable for one or more of the components in the feed stream. At least part of some of the components pass through the membrane to the other side of the membrane (the permeate side), thereby forming a permeate stream of the cell. The other components which do not pass the membrane, form the retentate stream of the cell.

For some components of the fluid, the membrane may be semi-permeable, i.e. a part of all the components in the feed stream will pass the membrane, the other part will not.

By selecting a membrane which is more permeable for hydrogen chloride as compared to the permeability for phosgene, the permeate of the cell will compromise more hydrogen chloride as compared to the feed, and less phosgene as compared to the feed. As such, a hydrogen chloride enriched and phosgene depleted permeate is obtained. The permeate being hydrogen chloride enriched and phosgene depleted is a gaseous stream.

The retentate, which may be liquid or gaseous, will comprise more phosgene as compared to the feed, and less hydrochloride as compared to the feed. As such, a hydrogen chloride depleted and phosgene enriched retentate is provided.

Optionally, a part of the retentate and/or the permeate may be recycled and blended with the initial fluid stream for feeding it back to the inflow side of the membrane separation unit.

The initial fluid stream fluid, optionally being gaseous, is provided through the at least one inflow means to the membrane separation unit. The first and the second fluid stream each leaves the membrane separation unit respectively through the first and the second effluent outflow means.

In case the membrane separation unit comprises only one separation cell, the initial fluid stream is used as feed of this one separation cell, the permeate of this cell providing the first fluid stream, and the retentate providing the second fluid stream.

In case the membrane separation unit comprises more than one separation cell, these cells may be coupled to each other in parallel, i.e. the initial fluid stream is used as feed all separation cells, the permeates of these cells being combined to provide the first fluid stream, and the retentate of these cells being combined to provide the second fluid stream. Alternatively, these more than one cells may be coupled in series. In its most simple form, the initial fluid stream is used as feed the first cell of the N cells in series, the feed of each subsequent cell is the retentate of the previous cell. The first fluid is the combination of all permeates of the cells, whereas the second fluid stream is the retentate of the last cell in the series. Alternatively, the initial fluid stream is used as feed the first cell of the N cells in series, the feed of each subsequent cell is the retentate or the permeate of a previous cell. The first and second fluid streams are appropriate combinations of permeates and/or retentates of the cells at the ends of the series. Preferably, the first fluid stream is the combination of permeates of the cells at the ends of the series, whereas the second fluid stream is the combination of retentates of the cells at the ends of the series.

It is understood that more than one series of separation cells may be arranged in parallel, i.e. the initial fluid stream is used as feed the first separation cells of each series, and each of the series provide a part of the first and second fluid stream.

Optionally, in case the fluid is a gaseous phase, measures may be taken to avoid condensation of the gaseous fluids between subsequent cells. E.g. condensers or heaters may be provided between consecutive cells. Alternatively or additionally, the cells may also themselves be temperature controlled, e.g. be provided with a heating and/or cooling means.

As such a partial separation of phosgene and hydrogen chloride present in the initial fluid stream may be obtained.

Suitable membranes are ceramic, glass, carbon, metal, hybrid or polymeric membranes, the membrane being porous or non-porous. Preferably carbon based membranes, silicon carbide membranes, polyimide membranes, PEEK membranes, zeolite membranes or perfluoropolymer based membranes are used.

It is understood that also a membrane being more permeable for phosgene and less permeable for hydrogen chloride may be selected, providing a similar effect.

As the membrane or membranes used are more permeable for one component, preferably for hydrogen chloride, as compared to the permeability for the other components, preferably phosgene, the component for which the membrane is more permeable will pass more easily through the membrane. To improve the permeation of this component, preferably a pressure difference is applied between both sides of the membrane. This pressure difference is preferably in the range of 1 to 50 bara.

Possibly the pressure at the retentate side is above atmospheric, while the pressure at the permeate side of the membrane is sub-atmospheric, i.e. a vacuum is applied to the permeate side. A pressure above atmospheric in the range of 1.2 to 4 bara is preferably applied to the retentate side, whereas at the permeate side, a vacuum of 0.1 to 0.9 bara is preferably applied.

Possibly a sweep gas is provided to the permeate side of the membrane or membranes to facilitate the evacuation of the components having passed through the membrane. Suitable sweep gasses are nitrogen, steam or other gasses such as monochlorobenzene when working under reduced pressure. Additional advantages may be gained from the use of one or more sweep gasses which act as a solvent for one or more of the components of the overall production process.

According to some embodiments, the initial fluid stream may be a liquid stream.

According to some embodiments, the second fluid stream may be a liquid stream.

The initial fluid stream being a liquid stream, may further comprise other components in liquid form, e.g. water or other solvents, e.g. monochlorobenzene. 1,2-dichlorobenzene, 1,3-dichlorobenzene or 1,4-dichlorobenzene. It is to be understood that in such industrial process streams still further components may be present e.g. phenyl isocyanate.

Depending on the process settings and the type of membrane used in the membrane separation unit, these other liquid components may be present in the first and/or the second fluid stream obtained by the method.

In case water is present in the initial fluid stream, the hydrogen chloride is likely to be present in its acid form, i.e. hydrochloric acid.

According to some embodiments, the initial fluid stream may be a gaseous stream.

According to some embodiments, the second fluid stream may be a gaseous stream.

The initial fluid stream being a gaseous stream, may further comprise other components in gaseous form, e.g. water vapor or other solvents in gaseous form, e.g. monochlorobenzene. 1,2-dichlorobenzene, 1,3-dichlorobenzene or 1,4-dichlorobenzene.

Depending on the process settings and the type of membrane used in the membrane separation unit, these other gaseous components may be present in the first and/or the second fluid stream obtained by the method.

Most preferred, a membrane is selected which is substantially impermeable for either phosgene or hydrogen chloride. A partial or complete removal of the component for which the membrane is substantially impermeable may be obtained.

Typical membranes are ceramic, glass, carbon, metal, hybrid or polymeric membranes, the membrane being porous or non-porous. Preferably carbon based membranes, silicon carbide membranes, polyimide membranes, PEEK membranes, zeolite membranes, any perfluoropolymer-based membranes or polydimethylsiloxane (PDMS) membranes are used.

According to a second aspect of the present invention, a process for the conversion of an amine to the corresponding isocyanate component by phosgenation of said amine is provided. The process comprising the steps of
  Providing a reaction mixture comprising an amine and phosgene to a phosgenation reactor;
  at least partially converting the amine and the phosgene in said reaction mixture into the corresponding isocyanate component and hydrogen chloride, thereby providing a liquid isocyanate stream comprising said isocyanate component, phosgene and hydrogen chloride;
  removing at least part of said phosgene and at least part of said hydrogen chloride from said liquid isocyanate stream, thereby providing an initial fluid stream comprising phosgene and hydrogen chloride;
  evacuating at least part of the hydrogen chloride from said initial fluid stream, said evacuation comprises a process according to the first aspect of the present invention.

The process may be applied in processes for converting virtually all amine to its corresponding isocyanate through phosgenation. The processes are suitable for use in the phosgenation of a.o. toluene diamine (TDA) to toluene diisocyanate (TDI), hexamethylene diamine (HDA) to hexamethylene diisocyanate (HDI), isophorone diamine (IPDA) to isophorone diisocyanate (IPDI), methylenedicyclohexylamine (H12MDA) to methylenedicyclohexylisocyanate (H12MDI). It is understood that the amines mentioned may be used in crude form, i.e. as mixtures of isomers and other components obtained by the production process to provide the amine as well known in the art.

Preferably the amine is crude methylene-bridged polyphenyl polyamines (also referred to as MDA). This crude methylene-bridged polyphenyl polyamines typically is a mixture of the isomers of methylene diphenylene diamine (so called 2,2'MDA, 2,4'MDA and 4,4'MDA), in combination with methylene-bridged polyphenyl polyamines comprising more than 2 phenyl and more than 2 amine groups in their structure. This crude methylene-bridged polyphenyl polyamines typically is prepared from aniline, or aniline derivatives, by reacting them with formaldehyde in the presence of a solution of a strong acid such as, for example, hydrochloric, sulfuric or phosphoric acid. Formaldehyde may be provided in various forms, preferably as an aqueous solution. Solid acid catalyzed processes are also known.

Preferably the phosgene and the hydrogen chloride, i.e. at least part of it, are removed from the liquid isocyanate stream as a gaseous mixture comprising phosgene and hydrogen chloride. This mixture obtained after the phosgenation of the amine and separated off from the liquid isocyanate stream, typically comprises 15 to 50 wt % phosgene, 30 to 80 wt % hydrogen chloride, and 0.01 to 40 wt % solvent, typically MCB. The solvent is used to facilitate the phosgenation of the amines in liquid form and is used to dissolve the amine and the phosgene before mixing and reacting these two components. Such gaseous mixture comprising phosgene and hydrogen chloride typically is provided at temperatures of above 75 deg C., typically in the range of −30 to 160 deg C. Typical pressure of the gaseous mixture is in the range of 2 to 40 bara.

According to some embodiments, the reaction mixture of an amine and phosgene further may comprise a solvent.

The solvent typically is inert in the reaction of amine and phosgene. Typically MCB is used.

According to some embodiments, the initial fluid stream comprising phosgene and hydrogen chloride further may comprise at least part of said solvent.

According to some embodiments, a process for the conversion of an amine to the corresponding isocyanate component by phosgenation of said amine, the process comprising the steps of Providing a reaction mixture comprising an amine and phosgene to a phosgenation reactor;

at least partially converting the amine and the phosgene in said reaction mixture into the corresponding isocyanate component and hydrogen chloride, thereby providing a liquid isocyanate stream comprising said isocyanate component, phosgene and hydrogen chloride;

removing at least part of said phosgene and at least part of said hydrogen chloride from said liquid isocyanate stream, thereby providing an initial fluid stream comprising phosgene and hydrogen chloride;

evacuating at least part of the hydrogen chloride from said initial fluid stream, said evacuation comprises a process according to the first aspect of the present invention, wherein the initial fluid stream is a gaseous stream.

According to some embodiments, the removing at least part of the phosgene and at least part of the hydrogen chloride from the liquid isocyanate stream may comprise removing at least part of said phosgene and at least part of said hydrogen chloride from said liquid isocyanate stream as a gaseous mixture;

at least partially condensing the gaseous mixture providing a liquid intermediate mixture and said initial fluid stream being a gaseous stream;

using said initial fluid stream being a gaseous stream to feed said membrane separation unit.

According to some embodiments, the second fluid stream of the membrane separation unit may be condensed and blended with the liquid intermediate mixture.

According to some embodiments, the removing at least part of the phosgene and at least part of the hydrogen chloride from the liquid isocyanate stream may comprise removing at least part of said phosgene and at least part of said hydrogen chloride from said liquid isocyanate stream as a gaseous mixture;

at least partially condensing the gaseous mixture providing a liquid intermediate mixture and a gaseous intermediate mixture;

distilling and/or stripping and/or washing with a solvent of the gaseous intermediate mixture and/or the liquid intermediate mixture to provide a gaseous vent mixture comprising hydrogen chloride and phosgene;

using the gaseous vent mixture as the initial fluid stream to feed said membrane separation unit.

According to some embodiments, evacuating the at least part of the hydrogen chloride from the gaseous mixture may comprise using the gaseous mixture as the initial fluid stream fed to the membrane separation unit.

According to some embodiments, condensing may include cooling the gaseous mixture to a temperature in the range of 60 to 20 deg C.

According to some embodiments, condensing may include cooling the gaseous mixture to a temperature in the range of 20 to −40 deg C.

Hence the cooling may be conducted in subsequent stages.

The use of one or more membrane separation units may result in the increase of the apparent condensation point or partial vapour pressure of phosgene in the product stream or streams which are cooled to condense phosgene.

Possibly, the volume of gaseous streams to be compressed can be reduced.

Possibly, the use of membrane separation unit or units may avoid partially or completely the need of an absorption fluid.

According to some embodiments, the first fluid stream of the membrane separation unit may be distilled and/or stripped and/or washed with a solvent further reducing the content of phosgene in the first fluid stream.

In case a solvent, such as MCB is used, the first fluid stream may comprise solvent, optionally only traces of the solvent and can be substantially free of phosgene. This first fluid stream, optionally after distillation, washing and/or stripping, may be compressed and optionally cooled to pressurize the hydrogen chloride, while condensing the solvent together with part of the hydrogen chloride.

Traces of solvent is to be understood as comprises the fluid an amount of solvent in the range of 1 ppm to 1 w %, preferably 1 ppm to 100 ppm. Substantially free of phosgene means that the fluid comprises 1 ppm to 0.1 w %, preferably 1 ppm to 100 ppm of phosgene.

Using the process according to the present invention for the conversion of an amine to the corresponding isocyanate component may result in a stream of substantially pure hydrogen chloride.

Substantially pure hydrogen chloride means that the fluid comprises 1 ppm to 0.1 w %, preferably 1 ppm to 100 ppm of phosgene.

This substantially pure hydrogen chloride may be used in other chemical processes run on the same chemical plant. Alternatively this hydrogen chloride may be transported to remote operations, or may be used to provide hydrochloric acid, by combining the hydrogen chloride with water. As an example, in case the isocyanate made is methylene diphenylene diisocyanate (MDI), the hydrogen chloride may be recycled to the production facility (as gaseous hydrogen chloride or as liquid hydrochloric acid) where aniline and formaldehyde are condensed to methylene diphenylene diamine, the precursor amine of the present process for the conversion of an amine to the corresponding isocyanate component by phosgenation of said amine. It is known, for example, to add gaseous hydrogen chloride to aniline/water mixtures.

Most preferred, the second gaseous stream comprises the phosgene present in the initial fluid stream, together with remainders of optional solvent in case the phosgenation reaction is carried out in presence of solvent, e.g. MCB. This gaseous stream may be recycled to the conversion of amine and phosgene to isocyanate and hydrogen chloride.

The advantage of the processes according to the present invention is that the clean up of the gaseous streams can be performed in a more economical and efficient way, using less energy. In comparison with prior art processes, the removal of at least part of the phosgene from the valuable hydrogen chloride effluent of the process through membrane separation does not require a significant amount of energy. For example compared to a process where the removal of the phosgene is carried out using distillation columns only, which requires a significant amount of energy to pump and cool the liquids and gasses in such columns.

The independent and dependent claims set out particular and preferred features of the invention. Features from the dependent claims may be combined with features of the independent or other dependent claims as appropriate.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

The same reference signs refer to the same, similar or analogous elements in the different figures.

The present invention will be described with respect to particular embodiments.

It is to be noticed that the term "comprising", used in the claims, should not be interpreted as being restricted to the means listed thereafter; it does not exclude other elements or steps. It is thus to be interpreted as specifying the presence of the stated features, steps or components as referred to, but does not preclude the presence or addition of one or more other features, steps or components, or groups thereof. Thus, the scope of the expression "a device comprising means A and B" should not be limited to devices consisting only of components A and B. It means that with respect to the present invention, the only relevant components of the device are A and B.

Throughout this specification, reference to "one embodiment" or "an embodiment" are made. Such references indicate that a particular feature, described in relation to the embodiment is included in at least one embodiment of the present invention. Thus, appearances of the phrases "in one embodiment" or "in an embodiment" in various places throughout this specification are not necessarily all referring to the same embodiment, though they could. Furthermore, the particular features or characteristics may be combined in any suitable manner in one or more embodiments, as would be apparent to one of ordinary skill in the art.

The following terms are provided solely to aid in the understanding of the invention.

Except explicitly stated differently, when reference is made to w % or "weight percent" of a component, this figure refers to the weight of this component over the total weight of the fluid or product in which the component is present at that moment, the ratio being expressed as percentage.

Unless otherwise indicated, the term "bara" is a reference to the absolute pressure expressed in the unit "bar", wherein 1 bar equals 100 kPa and 0.987 atm.

Nothing is implied about the physical or chemical nature of chemical species, e.g. solvents, when said in or on the membrane.

Figure 1:
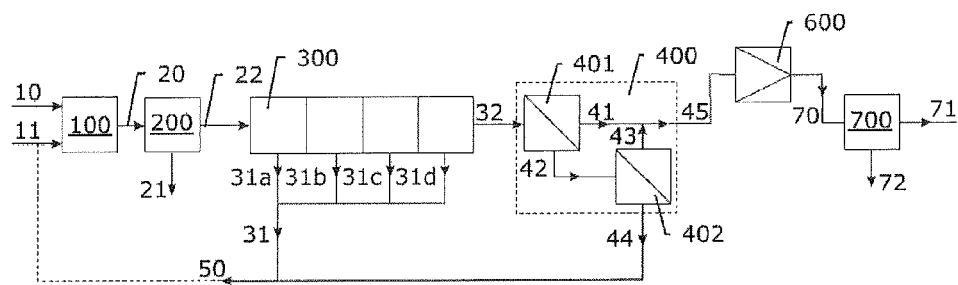
FIGS. 1, 2, 3 and 4 are schematic views of processes for the conversion of an amine to the corresponding isocyanate component according to the invention.

FIG. 1 shows schematically a process for the conversion of an amine, in particular MDA, to the corresponding isocyanate component, being MDI, by phosgenation of this amine.

A reaction mixture comprising MDA and phosgene is provided to a phosgenation reactor 100. This is done by providing MDA dissolved in MCB through stream 10 and phosgene dissolved in MCB through stream 11. Typically an excess of phosgene is provided in reactor 100. The reactor may be, as is known in the art, a series of consecutive reactors, through which the reaction mixture passes one after the other. At least part of the MDA is converted to MDI, thereby producing hydrogen chloride. At the end of the reaction in the reactor 100, a liquid isocyanate stream 20 comprising the isocyanate component, the excess or non reacted phosgene and hydrogen chloride is obtained.

The liquid isocyanate stream 20 is subjected to distillation and stripping to remove part of the solvent and residual traces of phosgene and HCl in reactor 200, thereby providing a gaseous mixture 22 comprising phosgene and hydrogen chloride, and part of the solvent being MCB. The isocyanate and the rest of the solvent MCB is recovered as stream 21.

The gaseous mixture 22 has a temperature typically 50 to 200° C. The gaseous mixture is cooled in a cooling train 300, where in consecutive stages, using ambient air cooling, ambient water cooling and cooling using a refrigerant, the temperature of the gaseous mixture is reduced to typically 100 to −35° C.

By cooling the gaseous mixture 22, the phosgene and the MCB condenses and is taken off as stream 31, being the combination of various streams obtained between the different cooling stages, i.e. streams 31a, 31b, 31c and 31d. In this stream 31, also some hydrogen chloride may be present.

At least part of the hydrogen chloride is evacuated from the cooled gaseous mixture 32 using a membrane separation unit 400, comprising two separation cells 401 and 402, being coupled in series.

In this membrane separation unit 400, the cooled gaseous mixture 32 is the initial fluid stream comprising phosgene and hydrogen chloride, which is fed to the membrane separation unit 400. In the first separation cell 401 of the membrane separation unit 400, this gaseous mixture 32 is separated in a permeate stream 41 and a retentate stream 42. The permeate stream 41 comprises hydrogen chloride and some residual phosgene and MCB.

Various kinds of materials such as ceramic, glass, carbon, metal, hybrid or polymers can be used as membrane material. The membrane may be porous or non-porous. The membrane separation unit or membrane system may comprise one or more modules, i.e. an element holding a membrane in a frame. The modules may be e.g. but not limited thereto, plate and frame module, spiral wound module, tubular module, capillary module or hollow fiber membrane.

The retentate stream 42 comprises phosgene, hydrogen chloride and MCB. In the second separation cell 402 of the membrane separation unit 400, this retentate stream 42 is separated in a permeate stream 43 and a retentate stream 44. The membrane used is similar or even identical to the one of the first cell 401.

As such, the cooled gaseous mixture 32, being the initial fluid stream comprising phosgene and hydrogen chloride of the membrane separation unit 400, is separated in first gaseous stream 45, being a hydrogen chloride enriched and phosgene depleted stream obtained by combining the permeate streams 41 and 43, and in a second gaseous stream being the retentate stream 44.

This second gaseous stream 44 may be further condensed and combined with stream 31 to provide a phosgene-rich fluid 50 further comprising hydrogen chloride and MCB. This phosgene rich stream 50 may be recycled to the phosgenation step in reactor 100, optionally after further treatment.

The first gaseous stream 45 may be further used, e.g. by compression in compressor 600, after which the traces of MCB can be removed from the compressed hydrogen chloride rich steam 70, e.g. by condensing in condenser 700 to provide substantially solvent free hydrogen chloride gas 71 and a combined hydrogen chloride-MCB stream 72. Compositions of various streams may be as in table I.

TABLE I

| | Stream # | | | | | |
|---|---|---|---|---|---|---|
| | 20 | 22 | 31 | 32 | 44 | 45 |
| HCl | 5-10 w % | 20-45 w % | 0-5 w % | 45-70 w % | 5-20 w % | 80-100 w % |
| Phosgene | 5-25 w % | 15-45 w % | 20-40 w % | 20-40 w % | 50-80 w % | 0-20 w % |
| Solvent | 35-65 w % | 40-70 w % | 55-75 w % | 10-20 w % | 15-30 w % | 0-10 w % |
| Isocyanate | 15-20 w % | | | | | |

Figure 2:
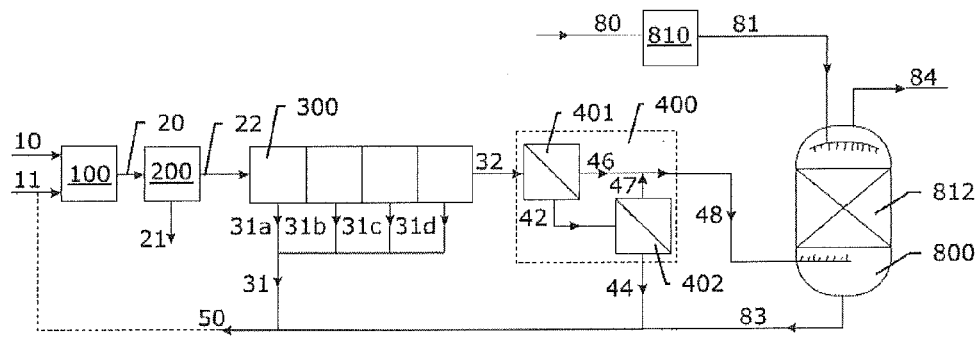

An alternative process is illustrated schematically in FIG. 2. The same reference signs refer to similar apparatuses and product streams as in FIG. 1. The permeates 46 and 47 comprises some traces of phosgene. The hydrogen chloride enriched, phosgene depleted gaseous stream 48, being the combination of these two permeate streams 46 and 47, is subjected to a washing process in wash column 800. In this column, MCB (80) being cooled in cooler 810 to a temperature of about 20 to −25 deg C., runs as cooled MCB 81 in counter current to the gaseous stream 48 through the column 800, which may be provided by a means for intimately contacting the liquid MCB and the gaseous stream 48, as known in the art, e.g. a packed bed 812. In the sump of the wash tower 800, a solvent stream 83 with phosgene taken out of the gaseous stream 48 is obtained, which may be used separately, as shown in FIG. 2 in a combined stream with the phosgene enriched stream 44 and/or the condensed phosgene stream 31 as a recycle stream 50 to the phosgenation step in reactor 100. The washed hydrogen chloride enriched stream 84 may be sufficiently pure to be taken out of the process as byproduct, or may be fit for recycle to other processes, or may further be subjected to the compression and condensing steps as discussed in FIG. 1.

Figure 3:
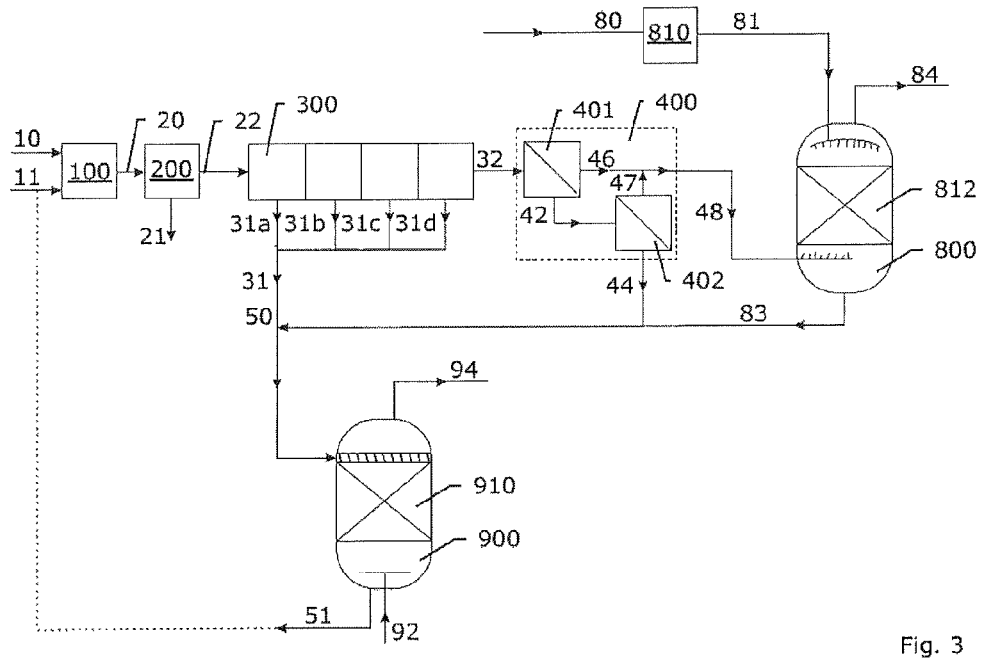

A further alternative process is illustrated schematically in FIG. 3. The same reference signs refer to similar apparatuses and product streams as in FIGS. 1 and 2. This phosgene rich stream 50 may be treated in a stripping column 900, e.g. comprising a trickle bed zone or a packed zone 910, to further remove hydrogen chloride from the liquid mixture of MCB and phosgene. Stripping gas 92, e.g. gas of the phosgene production facility comprising CO and $N_2$, is forced in counter follow through the descending liquid 50 in column 900. The sump of the column 900 provided an MCB-phosgene mixture 51 which is more hydrogen chloride depleted as compared to the phosgene rich stream 50. At the top of the column 900, the stripping gas enriched with hydrogen chloride gas 94 is removed from the column. This gas may be combined with gaseous stream 48 before it enters in wash column 800, or may be combined with washed hydrogen chloride enriched stream 84, or may be used without being mixed. Alternatively, the gas 94 may be further depleted from phosgene by a membrane separation according to the invention.

It is understood that this stripping step can be performed in processes not comprising the washing step performed in wash column 800 and explained in FIG. 2.

Figure 4:
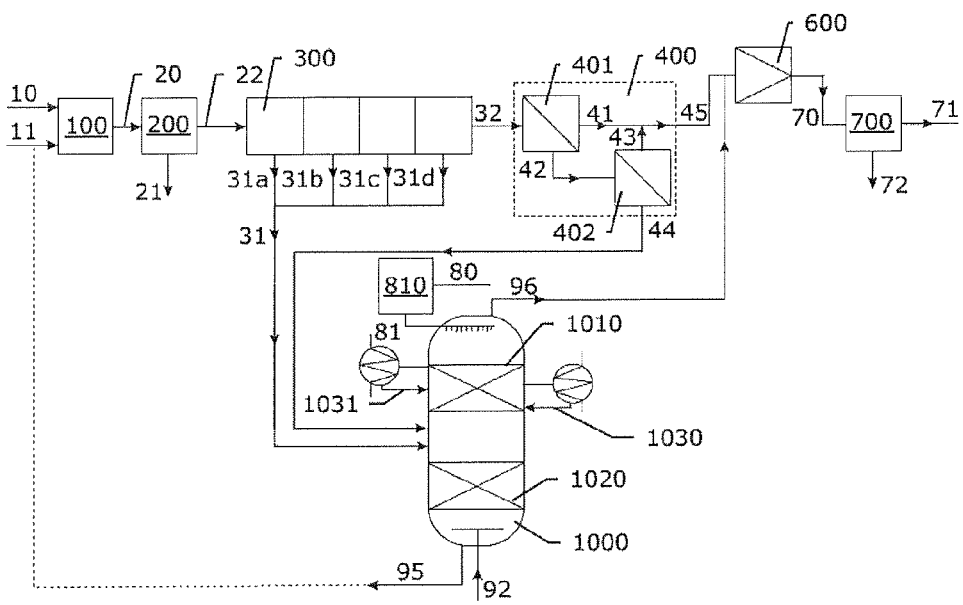

A further alternative process is illustrated schematically in FIG. 4. The same reference signs refer to similar apparatuses and product streams as in FIGS. 1, 2 and 3.

The second gaseous stream being the retentate stream 44 is subjected to a washing operation, while the stream 31, being condensed phosgene and MCB and also including some hydrogen chloride is subjected to a stripping operation. This washing and stripping is performed in one tower 1000, comprising two separate beds 1010 and 1020, the first bed 1010 located upstream the second bed 1020 in the direction of liquid running from the top to the bottom of tower 1000.

The two streams 44 and 31 are fed to the tower 1000 between the two beds 1010 and 1020. At the top of the tower 1000, cold solvent 81 (MCB) is fed to the tower 1000, similar as explained in FIG. 2 for wash column 800. The gaseous fluid of stream 44 will run in counter current compared to the descending cold solvent 81. The intimate contact between the solvent running downwards and the gas flowing upward through bed 1010 will cause the gas of stream 44 to be washed. As shown, intermediate cooling 1030 and 1031 may be foreseen to take out the energy released by the dissolving of phosgene in the solvent. The descending washing liquid is combined with the liquid feed stream 31 and will further run downwards the second bed 1020. At the bottom of the tower 1000, stripping gas 92 is fed to the tower, similar as explained in FIG. 3 for stripping column 900. The stripping gas will strip off hydrogen chloride out of the liquid running down the bed 1020. The hydrogen chloride enriched stripping gas will flow along with the gaseous fluid of stream 44 through the bed 1010 upwards the tower, and hence is washed to remove traces of phosgene.

Hence at the sump of the tower 1000, a liquid mixture of solvent 80 enriched with phosgene from the washing operation in bed 1010 and depleted from hydrogen chloride because of the stripping operation in bed 1020, is obtained. As such a mixture 95 of phosgene and solvent (MCB) is obtained, which may be recycled to the phosgenation reactor 100. Optionally, the fresh phosgene to be fed to the phosgenation reaction 100 may be mixed in the sump of the tower 1000, such that the mixture 95 of phosgene and solvent (MCB) provides the complete feed stream 11.

At the top of tower 1000, a gaseous fluid 96 enriched in hydrogen chloride is obtained which e.g. may be combined with stream 45. Alternatively, this gaseous fluid 96 may be treated separately from the gaseous stream 45.

Figure 5:
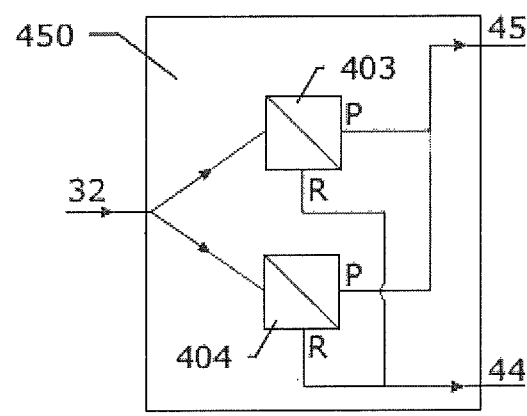
FIGS. 5, 6 and 7 show schematically alternative arrangements of separation cells in a membrane separation unit as used in accordance with the present invention.
Figure 6:
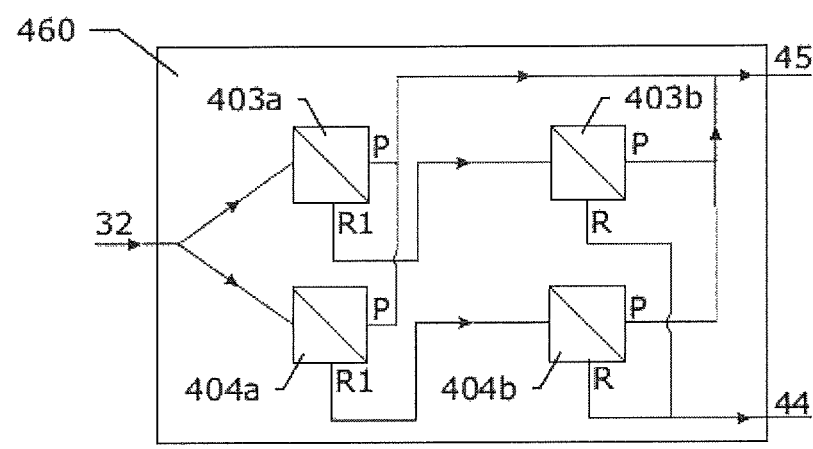
Figure 7:
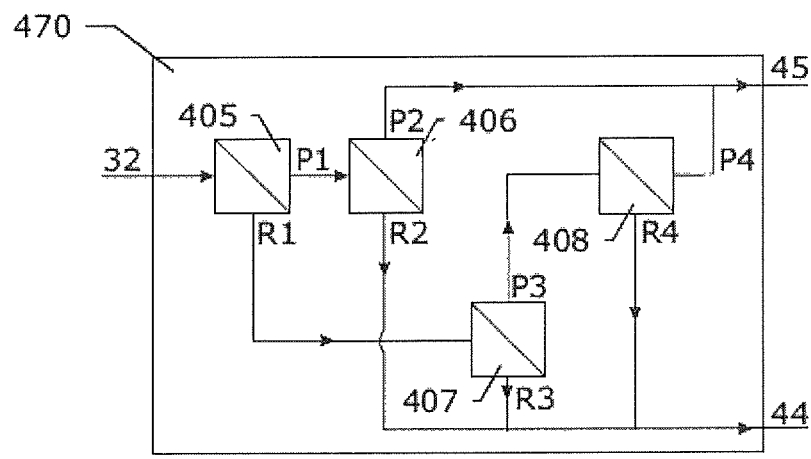

In the FIGS. 1 to 4, a process was described where the membrane separating unit 400 comprised two separation cells being arranged in series. As shown in FIGS. 5, 6 and 7, also other arrangements of separation cells within the membrane separation unit 400 may be used. In FIG. 5, two separation cells 403 and 404 are arranged in parallel in a membrane separation unit 450. Each cell 403 and 404 is fed with a part of the cooled gaseous mixture 32 being the initial fluid stream comprising phosgene and hydrogen chloride. The retentates R are combined to provide the second fluid stream 44 being phosgene enriched and hydrogen chloride depleted in comparison with the initial feed stream 32. The permeates P are combined to provide the first fluid stream 45 being phosgene depleted and hydrogen chloride enriched in comparison with the initial feed stream 32.

In FIG. 6, two series of separation cells 403a and 403b, respectively 404a and 404b are arranged in parallel in a membrane separation unit 460. Each first cell 403a and 404a is fed with a part of the cooled gaseous mixture 32 being the initial fluid stream comprising phosgene and hydrogen chloride. The retentates R1 of these first cells 403a respectively 404b, are used to feed the second cell 403b respectively 404b in the series. The retentates R of these second cells are combined to provide the second fluid stream 44 being phosgene enriched and hydrogen chloride depleted in comparison with the initial feed stream 32. The permeates P of all the cells 403a, 403b, 404a and 404b are combined to provide the first fluid stream 45 being phosgene depleted and hydrogen chloride enriched in comparison with the initial feed stream 32.

As shown in FIG. 7, also other combinations of separation cells being arranged in a combination of in parallel and in series may be used.

The cooled gaseous mixture 32 being the initial fluid stream comprising phosgene and hydrogen chloride is fed to separation cell 405 of a membrane separation unit 470, where the mixture is divided in a retentate R1 and a permeate P1 comprising hydrogen chloride and a minor amount of phosgene.

The permeate P1 is fed to a second separation cell 406, arranged in series with the cell 405. The permeate P1 is divided in a retentate R2 and a permeate P2 which is substantially free of phosgene.

The retentate R1, comprising phosgene end hydrogen chloride is fed to a third separation cell 407, also arranged in series with the cell 405. The retentate R1 is divided in a retentate R3 and a permeate P3.

The permeate P3 in its turn is fed to a fourth separation cell 408, arranged in series with the cell 407. The permeate P3 is divided in a retentate R4 and a permeate P4 which is substantially free of phosgene.

The retentates R2, R3 and R4 are combined to provide the phosgene enriched, hydrogen chloride depleted stream 44, whereas the permeates P2 and P4 are combined to provide the phosgene depleted, hydrogen chloride enriched stream 45.

It is well understood by the skilled person that arrangements of various separation cells can be chosen to obtain the purity of the first stream 45 and second stream 44.

Figure 8A:
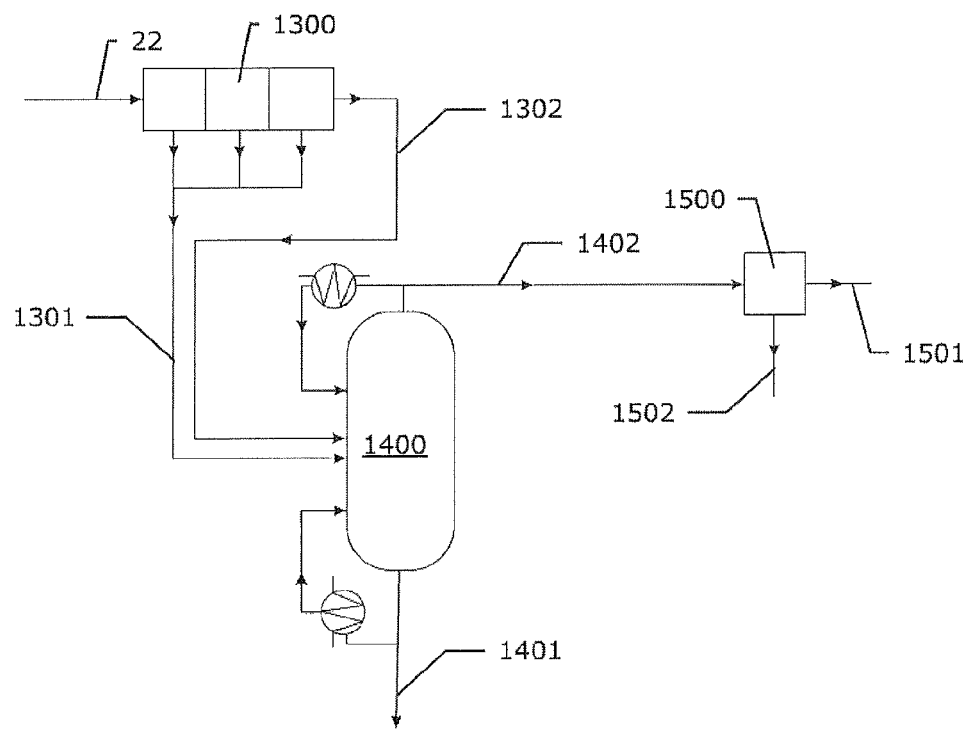
FIGS. 8 to 12 are schematically views of alternative processes or parts of processes for the conversion of an amine to the corresponding isocyanate component according to the invention.
Figure 8B:
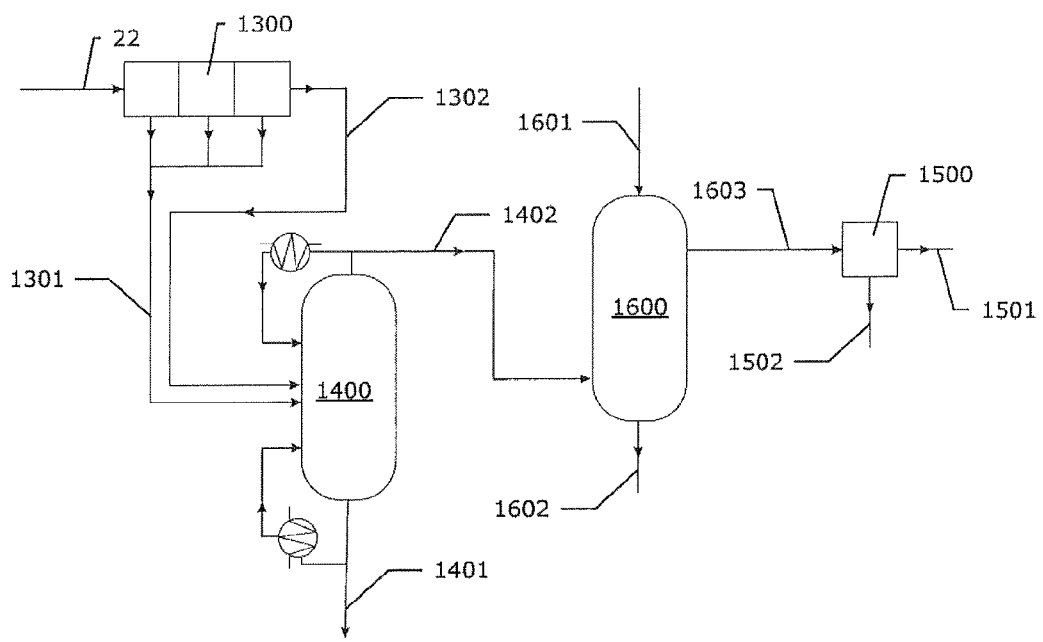
Figure 8C:
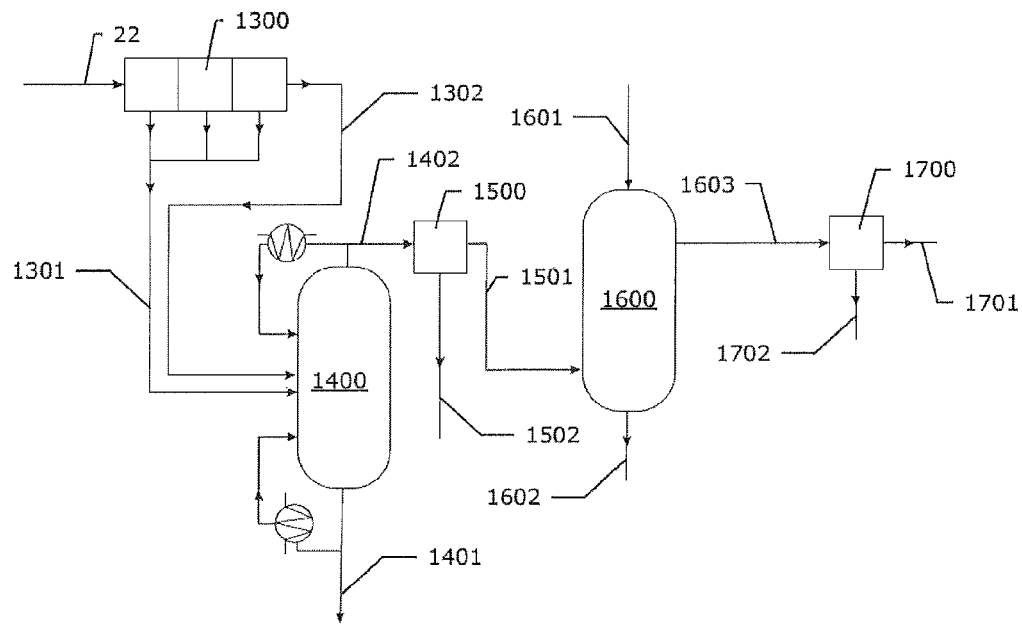

FIGS. 8a, 8b and 8c show schematically alternative processes for the separation of a gaseous stream comprising phosgene and HCl, originating from the conversion of an amine, in particular MDA, to the corresponding isocyanate component, being MDI, by phosgenation of this amine. This process comprises the consecutive distillation of phosgene, HCl and solvent (such as MCB) gaseous and liquid streams, after which the gaseous HCl stream, comprising some phosgene and optionally solvent, is washed with said solvent to remove partially or completely the remaining phosgene. Details of such process are set out in EP1575906A1.

A gaseous mixture 22 is cooled to at least partially condense the phosgene in the mixture 22, by means of one or a number of consecutive cooling means in condensing unit 1300. The condensate 1301 and the uncondensed mixture 1302 are fed to a distillation column 1400. Optionally, the condensate 1301 and the uncondensed mixture 1302 may be fed to the column 1400 as a two phase stream.

The liquid bottom stream 1401 of the distillation column 1400 is partially reboiled, the other part is recycled to the reaction process of reacting phosgene and an amine to provide the corresponding isocyanate and HCl. The top gaseous stream 1402 is partially condensed and brought back to the top of the distillation column 1400. As shown in FIG. 8a, the other part of the top gaseous stream 1402 may be treated using a membrane separating unit 1500, being identical to the membrane separation unit 400 of FIGS. 1 to 4, one of the membrane separation units 450, 460 or 470 as shown in FIGS. 5, 6 respectively 7, or any alternative set up of such membrane separation unit.

The gaseous HCl stream 1501 may be sufficiently pure to be taken out of the process as byproduct, or may be fit for recycle to other processes, or may further be subjected to the compression and condensing steps as discussed in FIG. 1. The phosgene enriched stream 1502 may be recycled to the phosgenation process, e.g. by first condensing the stream and recycling the condensed stream together with liquid stream 1401.

As shown in FIG. 8b, the other part of the top gaseous stream may be washed in wash column 1600 with solvent stream 1601, washing out part of the remaining phosgene to provide a phosgene/solvent stream 1602. This stream 1602 may be recycled to the phosgenation process along with stream 1401. The gaseous HCl stream 1603 at the top of the wash column 1600 may be treated using a membrane separating unit 1500, being identical to the membrane separation unit 400 of FIGS. 1 to 4, one of the membrane separation units 450, 460 or 470 as shown in FIGS. 5, 6 respectively 7, or any alternative set up of such membrane separation unit.

The gaseous HCl stream 1501 may be sufficiently pure to be taken out of the process as byproduct, or may be fit for recycle to other processes, or may further be subjected to the compression and condensing steps as discussed in FIG. 1. The phosgene enriched stream 1502 may be recycled to the phosgenation process, e.g. by first condensing the stream and recycling the condensed stream together with liquid stream 1401.

As shown in FIG. 8c, the other part of the top gaseous stream 1402 may be treated using a membrane separating unit 1500, being identical to the membrane separation unit 400 of FIGS. 1 to 4, one of the membrane separation units 450, 460 or 470 as shown in FIGS. 5, 6 respectively 7, or any alternative set up of such membrane separation unit.

The gaseous HCl stream 1501 may be washed in wash column 1600 with solvent stream 1601, washing out part of the remaining phosgene to provide a phosgene/solvent stream 1602. This stream 1602 may be recycled to the phosgenation process along with stream 1401. The gaseous HCl stream 1603 at the top of the wash column 1600 may be treated using a membrane separating unit 1700, being identical to the membrane separation unit 400 of FIGS. 1 to 4, one of the membrane separation units 450, 460 or 470 as shown in FIGS. 5, 6 respectively 7, or any alternative set up of such membrane separation unit.

The gaseous HCl stream 1701 may be sufficiently pure to be taken out of the process as byproduct, or may be fit for recycle to other processes, or may further be subjected to the compression and condensing steps as discussed in FIG. 1. The phosgene enriched streams 1502 and/or 1702 may be recycled to the phosgenation process, e.g. by first condensing the stream and recycling the condensed stream together with liquid stream 1401.

Figure 9:
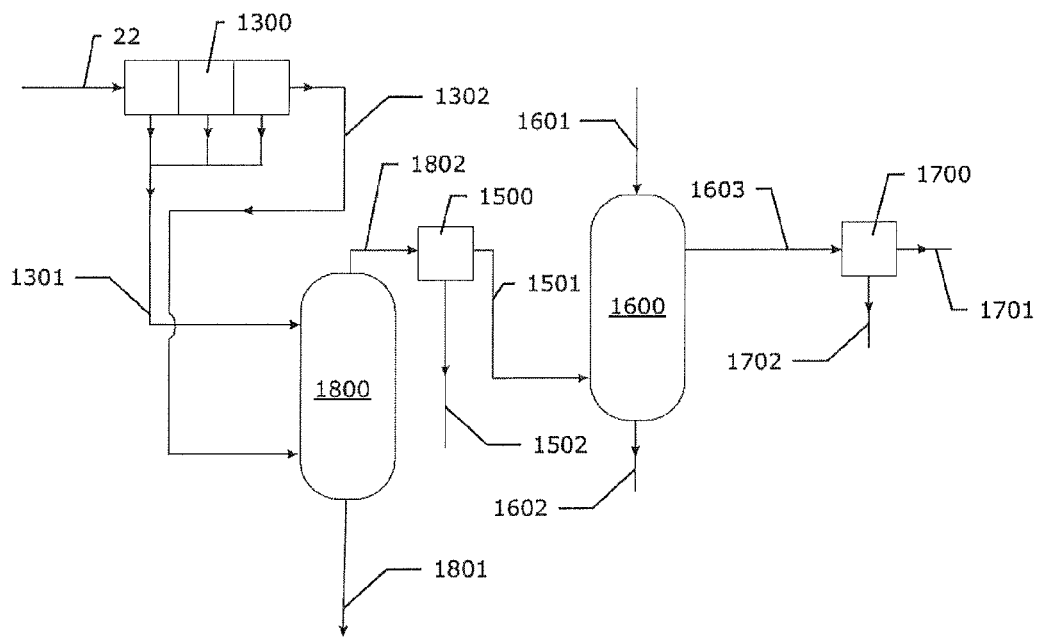

In an alternative process, the distillation column 1400 is replaced by a stripping column 1800 as shown in FIG. 9. The liquid phosgene/solvent mixture 1303 is provided to the top of the stripping column 1800, whereas the non condensed stream 1302 is used as stripping gas in this stripping column 1800. The bottom stream 1801 can be recycled in an identical or similar way as was set out for stream 1401 in FIGS. 8a, 8b and 8c.

The gaseous top stream 1802 of the stripping column can be used identically as gaseous top stream 1402 in FIG. 8a, FIG. 8b or FIG. 8c (as shown in FIG. 9).

Figure 10:
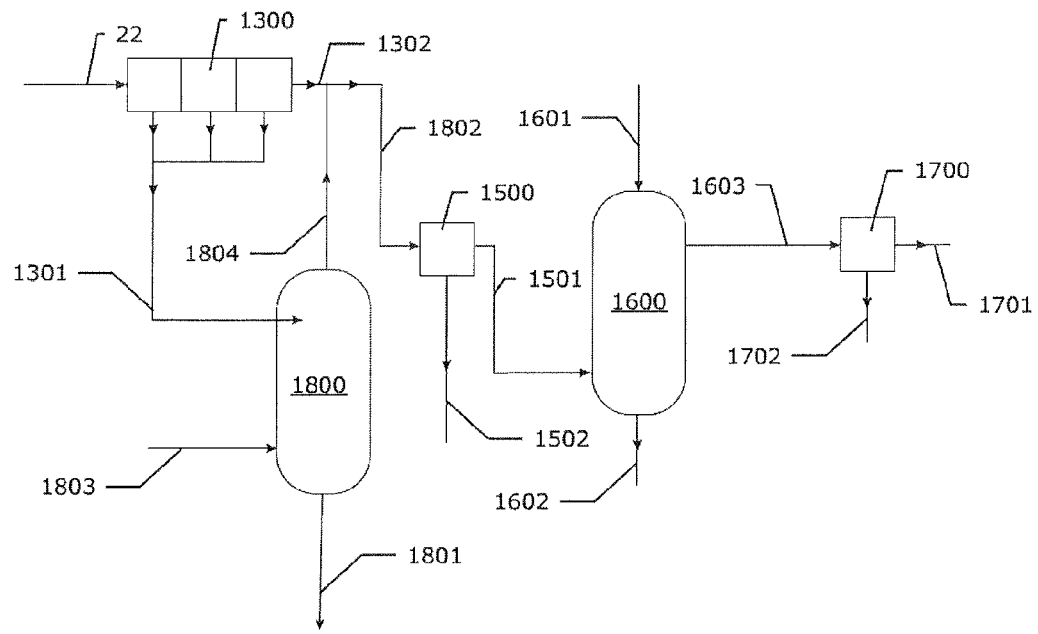

Alternatively, an inert gas stream 1803 can be used to strip the liquid stream 1301. This can be in addition to the use of gaseous stream 1302, or, as shown in FIG. 10, the inert gas and the stripped components, together forming stripper top stream 1804, can be combined with the gaseous stream 1302 to form the gaseous stream 1802, before its further treatment used identically as gaseous top stream 1402 in FIG. 8a, FIG. 8b or FIG. 8c (as shown in FIG. 10).

Figure 11:
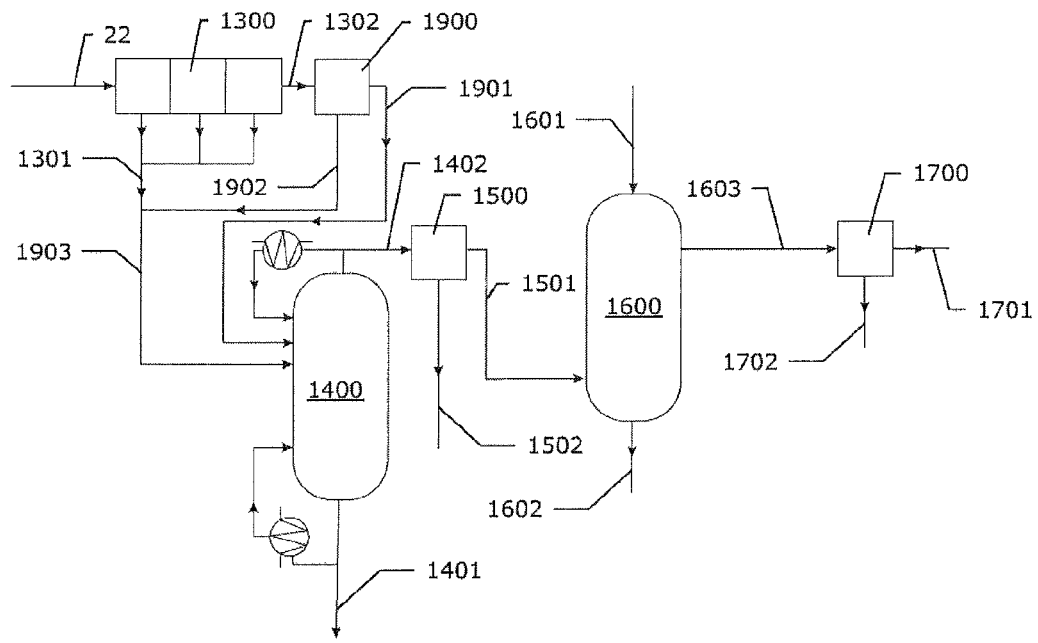

In an alternative process as shown in FIG. 11, the gaseous stream 1302 is first subjected to a membrane separation unit 1900, before its gaseous permeate stream 1901 is provided to the distillation column 1400. The membrane separating unit 1900 may be identical to the membrane separation unit 400 of FIGS. 1 to 4, one of the membrane separation units 450, 460 or 470 as shown in FIGS. 5, 6 respectively 7, or any alternative set up of such membrane separation unit.

The retentate stream 1902 of the membrane separation unit 1900 may be combined with the liquid stream 1301 to provide a mixture 1903 which is distilled in column 1400.

The process further may comprise all elements of the processes as shown in FIG. 8a, FIG. 8b or FIG. 8c (the latter is shown in FIG. 11).

Alternatively, the streams 1901 and/or 1903 may be provide to a stripping column 1800, similarly as shown in FIGS. 9 and 10 for streams 1301 and/or 1302.

Figure 12:
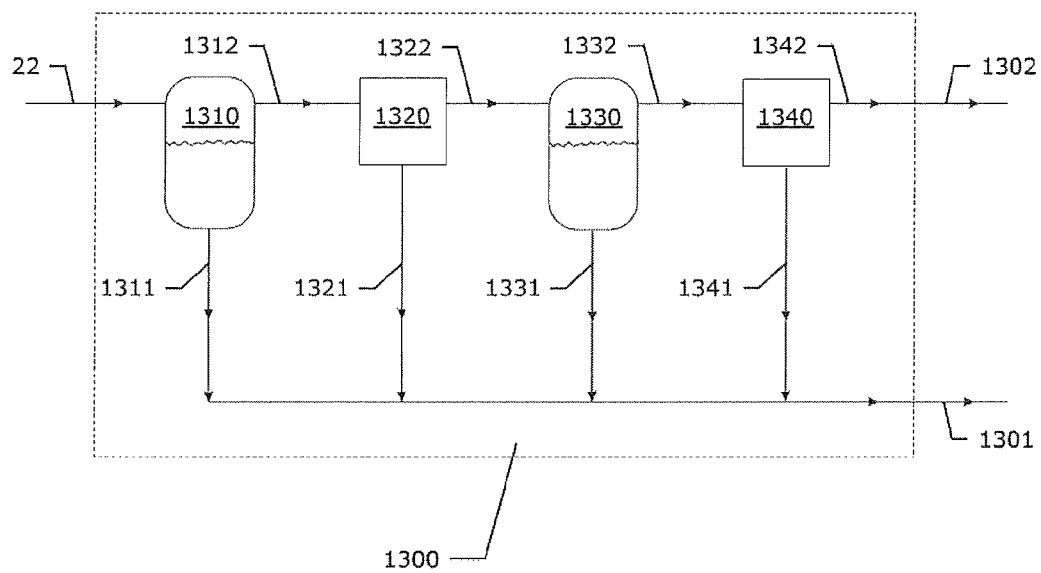

In further alternative processes, the streams 1301 and 1302 of the processes set out, may be provided by at least partially condensing a gaseous stream 22 comprising phosgene, HCl and a solvent using at least two consecutive condensing units. As shown in FIG. 12, the gaseous stream 22 comprising phosgene, HCl and a solvent, is partially condensed in a first condenser 1310 providing a condensate 1311 and a non condensed intermediate stream 1312. The non condensed intermediate stream 1312 may be subjected to a membrane separation unit 1320, the membrane separating unit 1320 may be identical to the membrane separation unit 400 of FIGS. 1 to 4, one of the membrane separation units 450, 460 or 470 as shown in FIGS. 5, 6 respectively 7, or any alternative set up of such membrane separation unit. The membrane separating unit 1320 provides a liquid phosgene enriched stream 1321 and a gaseous, HCl enriched stream 1322.

The gaseous stream 1322 comprising phosgene, HCl and a solvent, is partially condensed in a second condenser 1330 providing a condensate 1331 and a non condensed intermediate stream 1332. The non condensed intermediate stream 1332 may be subjected to a membrane separation unit 1340, the membrane separating unit 1340 being identical to the membrane separation unit 400 of FIGS. 1 to 4, one of the membrane separation units 450, 460 or 470 as shown in FIGS. 5, 6 respectively 7, or any alternative set up of such membrane separation unit. The membrane separating unit 1340 provides a liquid phosgene enriched stream 1341 and a gaseous, HCl enriched stream 1342.

The streams 1311, 1321, 1331 and 1341 together provide the liquid stream 1301 of the condensing unit 1300, whereas the gaseous, HCl enriched stream 1342 may provide the gaseous stream 1302 of the condensing unit 1300. These stream may further be combined with any of the processes as set out in relation to FIGS. 8a, 8b, 8c, 9, 10, 11 and its alternatives.

It is clear that also any other gaseous stream comprising phosgene, HCl and optionally one or more solvents may be treated in a similar or identical way. As an example a gaseous stream comprising phosgene and HCl originating from a process of a) formation of chloroformates from alcohols, phenol, substituted phenols, or b) formation of carbonates from alcohols, phenol, substituted phenols, or c) formation of carbamoyl chlorides from primary amines and secondary amines, or d) formation of sulphonyl isocyanates from sulphonamides, or e) formation of carbodiimides from substituted ureas.

Figure 13:
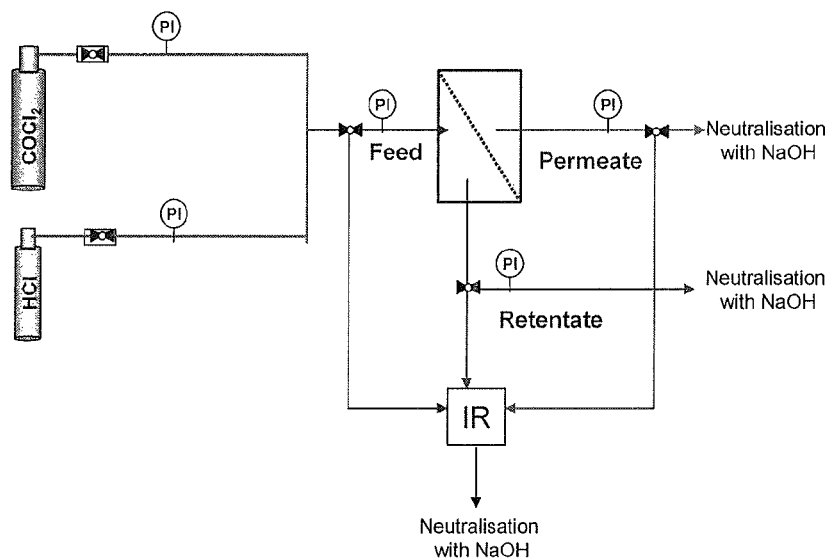
FIG. 13 is an experimental set up used to facilitate the demonstration of the processes according to the invention.

To demonstrate processes according to the invention different experiments were performed with a small membrane module based on polyimide hollow fibers, available from the company Evonik as Sepuran® green membrane modules. The tests were performed at room temperature for several hours. During the experiment, Phosgene and HCl gases were supplied from different gas cylinders. A drawing of the set-up used is also plotted in FIG. 13.

The different streams, feed, permeate and retentate, were analysed using infra red technique. The area of determined peak was measured and the concentration of the different gas calculated from the peak area.

EXPERIMENT 1

The phosgene and HCl content in the feed were respectively 49.4 wt % and 50.6 wt %, the feed pressure was set at 1.2 bara and the permeate was at atmospheric pressure. The HCl content in the retentate and the permeate were respectively 49.7 wt % and 60.5 wt %. These results demonstrate that HCl gas is going preferentially through the membrane while phosgene is preferentially retained.

EXPERIMENT 2

The phosgene and HCl content in the feed were respectively 49.4 wt % and 50.6 wt %, the feed pressure was set at 1.3 bara and the permeate was still at atmospheric pressure. The HCl content in the retentate and the permeate were respectively 48.1 wt % and 65.9 wt %. This mixture was treated using the same procedure and membrane described in Example 1. In comparison with the feed, the permeate is enriched in HCl, 65.9 wt %, while the retentate contains less HCl, 48.1 wt %.

EXPERIMENT 3

The phosgene and HCl content in the feed were respectively 49.4 wt % and 50.6 wt %, the feed pressure was set at 1.5 bara and the permeate was still at atmospheric pressure.

This mixture was treated using the same procedure and membrane described in Example 1. The permeate is enriched in HCl, 70.2 wt %, while the retentate contains less HCl, 43.2 wt %.

EXPERIMENT 4

The phosgene and HCl content in the feed were modified and were respectively 79.3 wt % and 20.7 wt %, the feed pressure was set at 1.5 bara and the permeate was at atmospheric pressure. This mixture was treated using the same procedure and membrane described in Example 1. The HCl content in the retentate and the permeate were respectively 18 wt % and 37 wt %.

EXPERIMENT 5

The phosgene and HCl content in the feed were modified and were respectively 20.9 wt % and 79.1 wt %, the feed pressure was set at 1.5 bara and the permeate was at atmospheric pressure. This mixture was treated using the same procedure and membrane described in Example 1. The HCl content in the retentate and the permeate were respectively 57 wt % and 89.5 wt %.

The results demonstrate that by using a membrane gas separation process, a decrease of the HCl content from the feed is obtained. A lower HCl content in the retentate and an enrichment of the HCl in the permeate are obtained. The best HCl removal are obtained with the highest HCl content in the feed and by using an in increased feed pressure.

TABLE 1

Stream compositions for the different experiments

| Experiment | Stream | Feed pressure (bara) | wt % HCl | wt % COCl2 | HCl removal from the feed (%) |
|---|---|---|---|---|---|
| 1 | Feed | 1.2 | 50.6 | 49.4 | / |
|   | Permeate |  | 60.5 | 39.5 | / |
|   | Retentate |  | 49.7 | 50.3 | 1.8 |
| 2 | Feed | 1.3 | 50.6 | 49.4 | / |
|   | Permeate |  | 65.9 | 34.1 | / |
|   | Retentate |  | 48.1 | 51.9 | 4.9 |
| 3 | Feed | 1.5 | 50.6 | 49.4 | / |
|   | Permeate |  | 70.2 | 29.8 | / |
|   | Retentate |  | 43.2 | 56.8 | 14.6 |
| 4 | Feed | 1.5 | 20.7 | 79.3 | / |
|   | Permeate |  | 37 | 63 | / |
|   | Retentate |  | 18 | 82 | 13 |
| 5 | Feed | 1.5 | 79.1 | 20.9 | / |
|   | Permeate |  | 89.5 | 10.5 | / |
|   | Retentate |  | 57 | 43 | 27.9 |

It is to be understood that although preferred embodiments and/or materials have been discussed for providing embodiments according to the present invention, various modifications or changes may be made without departing from the scope and spirit of this invention.

The invention claimed is:

1. A process for the conversion of an amine to a corresponding isocyanate component by phosgenation of said amine, the process comprising the steps of
providing a reaction mixture comprising an amine and phosgene to a phosgenation reactor;
at least partially converting the amine and the phosgene in said reaction mixture into the corresponding isocyanate component and hydrogen chloride, thereby providing a liquid isocyanate stream comprising said isocyanate component, phosgene and hydrogen chloride;
removing at least part of said phosgene and at least part of said hydrogen chloride from said liquid isocyanate stream thereby providing an initial gaseous stream comprising phosgene and hydrogen chloride;
evacuating at least part of the hydrogen chloride from said initial gaseous stream, said evacuation comprises a process comprising feeding said initial gaseous stream to a membrane separation unit having a retentate side and a permeate side, said membrane separation unit separating said initial gaseous stream into a first and a second gaseous stream.

2. The process according to claim 1, wherein removing at least part of said phosgene and at least part of said hydrogen chloride from said liquid isocyanate stream comprises
removing at least part of said phosgene and at least part of said hydrogen chloride from said liquid isocyanate stream as a gaseous mixture; and
at least partially condensing the gaseous mixture providing a liquid intermediate mixture and said initial gaseous stream.

3. The process according to claim 2, wherein the second gaseous stream of the membrane separation unit is condensed and blended with the liquid intermediate mixture.

4. The process according to claim 2, wherein said condensing includes cooling the gaseous mixture to a temperature in the range of 20 to 60° C.

5. The process according to claim 2, wherein said condensing includes cooling the gaseous mixture to a temperature in the range of −40 to 20° C.

6. The process according to claim 2, wherein the first gaseous stream of the membrane separation unit is distilled and/or stripped and/or washed with a solvent further reducing the content of phosgene in the first gaseous stream.

7. The process according to claim 1, wherein said reaction mixture of an amine and phosgene further comprises a solvent.

8. The process according to claim 7, wherein said initial gaseous stream further comprises at least part of said solvent.

9. The process according to claim 1, wherein removing at least part of said phosgene and at least part of said hydrogen chloride from said liquid isocyanate stream comprises:
removing at least part of said phosgene and at least part of said hydrogen chloride from said liquid isocyanate stream as a gaseous mixture;
at least partially condensing the gaseous mixture providing a liquid intermediate mixture and a gaseous intermediate mixture;
distilling and/or stripping and/or washing with a solvent of the gaseous intermediate mixture and/or the liquid intermediate mixture to provide a gaseous vent mixture comprising hydrogen chloride and phosgene.

10. The process according to claim 1, wherein said first gaseous stream comprises a hydrogen chloride enriched and phosgene depleted gaseous stream, and said second gaseous stream comprises a hydrogen chloride depleted and phosgene enriched stream.

11. The process according to claim 1, wherein the pressure at the retentate side is in the range of 1.2 to 4 bara and the pressure at the permeate side is in the range of 0.1 to 0.9 bara.

* * * * *